(12) United States Patent
Friedlander et al.

(10) Patent No.: US 8,100,584 B2
(45) Date of Patent: Jan. 24, 2012

(54) VOLTAGE MEASUREMENT IN AN IMAGING SYSTEM

(75) Inventors: Ariel Friedlander, Mequon, WI (US); Jonathan Richard Schmidt, Wales, WI (US); Thomas Louis Toth, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 135 days.

(21) Appl. No.: 12/603,261

(22) Filed: Oct. 21, 2009

(65) Prior Publication Data

US 2011/0091017 A1  Apr. 21, 2011

(51) Int. Cl.
*G01D 18/00* (2006.01)

(52) U.S. Cl. .................................. 378/207; 378/146

(58) Field of Classification Search .................. 378/146, 378/207, 111, 158, 159, 112, 4
See application file for complete search history.

(56) References Cited

U.S. PATENT DOCUMENTS

| 5,295,176 A | 3/1994 | Deslattes |
| 6,280,084 B1* | 8/2001 | Toth .............................. 378/207 |
| 6,454,460 B1 | 9/2002 | Ramanathan et al. |

* cited by examiner

*Primary Examiner* — Hoon Song
(74) *Attorney, Agent, or Firm* — Fletcher Yoder (57) ABSTRACT

Methods and systems are generally described for measuring a voltage used by an imaging system to generate radiation used in imaging. In embodiments, different datasets are acquired using different degrees of attenuation of the radiation. The differently attenuated datasets are processed to derive a ratio of the differential attenuation. The attenuation ratio is processed to derive a measure of the voltage used by the imaging system to generate the radiation used to acquire the different datasets.

18 Claims, 9 Drawing Sheets

VOLTAGE MEASUREMENT IN AN IMAGING SYSTEM

BACKGROUND OF THE INVENTION

The subject matter disclosed herein relates to imaging systems and, in particular, to the independent assessment of an operating voltage within an imaging system.

In the fields of medical imaging and security screening, non-invasive imaging techniques have gained importance due to benefits that include unobtrusiveness, convenience, and speed. In medical and research contexts, non-invasive imaging techniques are used to image organs or tissues beneath the surface of the skin. Similarly, in industrial or quality control (QC) contexts, non-invasive imaging techniques are used to examine parts or items for hidden defects that may not be evident from an external examination. In security screening, non-invasive imaging techniques are typically used to examine the contents of containers (e.g., packages, bags, or luggage) without opening the containers and/or to screen individuals entering or leaving a secure location.

A number of non-invasive imaging modalities exist today. A particular modality may be selected based upon the imaging context, such as the organ or tissue to be imaged, the spatial and/or temporal resolution desired, or upon whether structural or functional characteristics are of interest. Certain of these imaging modalities may operate by generating electromagnetic energy, such as X-rays, that is attenuated upon passing through subject or object being imaged. The differential attenuation of the X-rays or other energy may be used to formulate an image of the internal structures of the subject or object being imaged.

In certain contexts it may be desirable to periodically assess that the dose of X-rays or other energy being generated for imaging purposes corresponds to what has been specified by the operator of the imaging system. For example, regulations may specify that computed tomography (CT) or other X-ray generating imaging systems be periodically evaluated to confirm that the actual dose of X-rays generated by such an imaging system corresponds to the dose that is prescribed or specified. Such an evaluation may involve the measurement of certain operating parameters of the imaging system, such as the operating voltage (measured in kV) in the case of an X-ray based imaging system. Further, such evaluations should be conducted using instrumentation and/or techniques that are independent of the imaging system. That is, it is generally not deemed sufficient to rely solely on the instrumentation provided with the imaging system as such instrumentation may be subject to any defects or problems associated with the imaging system as a whole.

Further, in the case of X-ray based imaging systems, because of the high voltages involved, conventional, off-the-shelf measurement devices may be unsuitable to perform the desired measurement. As a result, techniques are typically employed that are obtrusive (requiring that the imaging system be opened) and time consuming and which utilize highly trained personnel, such as field engineers.

BRIEF DESCRIPTION OF THE INVENTION

In an embodiment, a method for measuring voltage is provided. The method includes the act of accessing a first scan dataset and a second scan dataset and of extracting a first region of interest from the first scan dataset and a second region of interest from the second scan dataset. A mean attenuation ratio is derived corresponding to the mean attenuation observed in the first region of interest relative to the mean attenuation observed in the second region of interest. The natural logarithm of the mean attenuation ratio is calculated and used to measure a voltage used to generate the first scan dataset and the second scan dataset.

In one embodiment, a voltage measurement system is provided. The voltage measurement system includes a processor-based system that in turn includes a memory storing executable instructions and processing circuitry configured to execute the executable instructions stored in the memory. The stored executable instructions include instructions which, when executed, cause acquisition of a first scan dataset and a second scan dataset by an imaging system. The first scan dataset is generated by transmitting radiation through a first attenuating medium and the second scan dataset is generated by transmitting radiation through a second attenuating medium. The stored executable instructions also include instructions which, when executed, cause processing of the first scan dataset and the second scan dataset to generate an attenuation ratio and processing of the attenuation ratio to generate a measurement of a voltage used by the imaging system to generate the first scan dataset and the second scan dataset.

In a further embodiment, a computer-readable medium is provided. The computer-readable medium includes computer executable code for measuring voltage. The executable code encodes instructions for processing a first set of scan data and a second set of scan data to derive an attenuation ratio. Each set of scan data is generated using the same prescribed voltage to generate X-rays but the X-rays used to generate first set of scan data are attenuated differently than the X-rays used to generate the second set of scan data. The executable code also encodes instructions for processing the attenuation ratio to derive an indirect measurement of the voltage used to generate the X-rays and for comparing the indirect measurement of the voltage to the prescribed voltage.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

The embodiments discussed below provide a technique for measuring a voltage used to generate X-rays in an imaging system. In particular, voltage may be measured as a function of X-ray attenuation using a known attenuating structure. More specifically, certain embodiments utilize an attenuating structure, such as a filter or phantom, that can be used to obtain attenuated image data using radiation generated at different voltage levels. The filter or phantom may be adjusted or removed so that image data may also be obtained for a different degree attenuation at the same voltage levels. For example, attenuation data may be obtained in the presence of a phantom and when the phantom is absent or may be obtained by passing the radiation through portions of a bowtie filter having different thicknesses. The differentially attenuated image data may be processed and mathematically fitted to derive respective measured voltage levels. The respective measure voltage levels may be compared to the prescribed voltage levels used to generate the image data to determine if the measured voltages generally correspond to their assigned or prescribed values.

Figure 1:
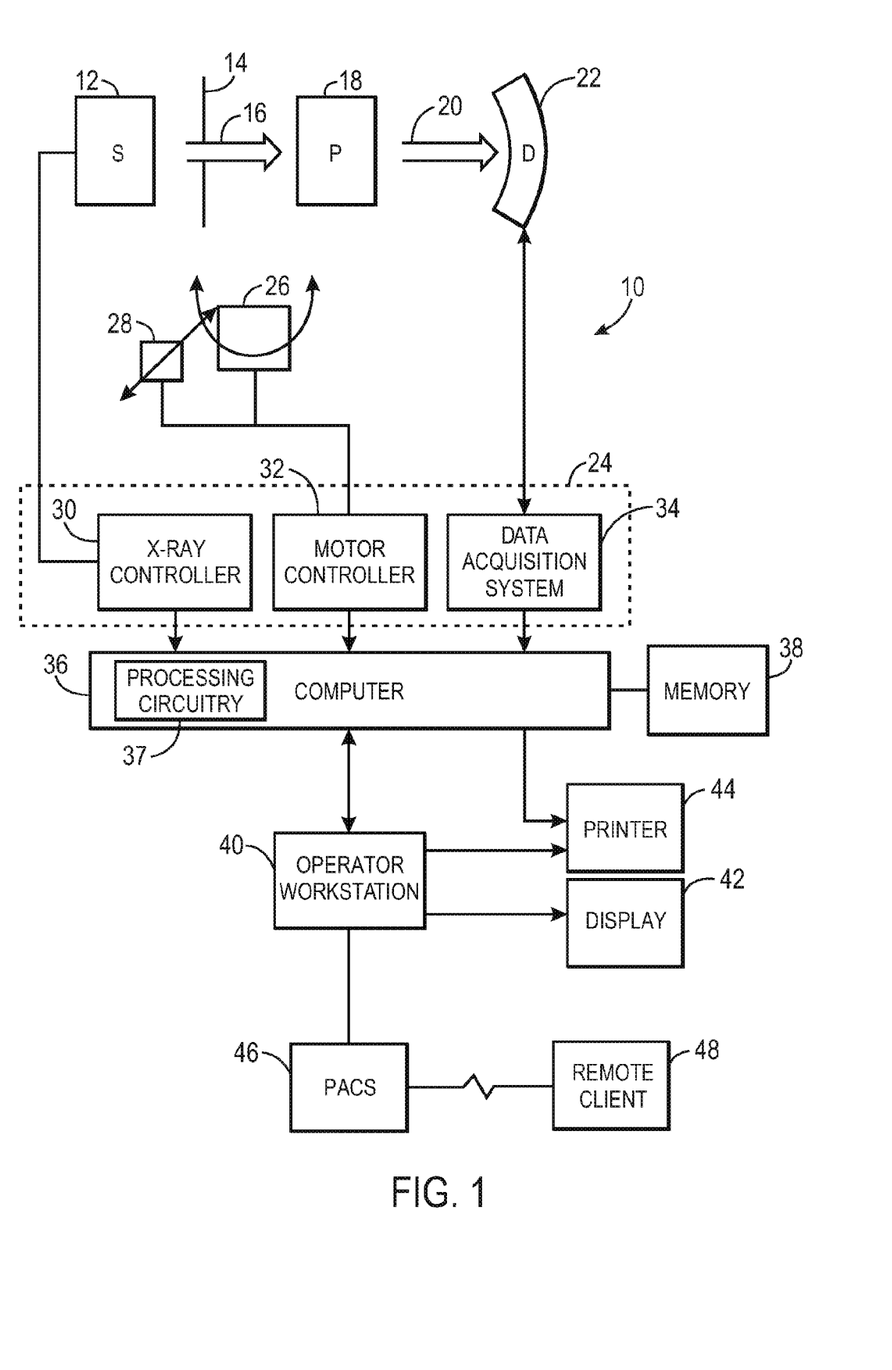
FIG. 1 is a diagrammatical illustration of an exemplary CT imaging system, in accordance with an embodiment of the present technique.

With the foregoing in mind, it may be beneficial to discuss embodiments of imaging systems that may incorporate the system and methods described herein before discussing these systems and methods in detail. With this in mind, and turning now to the figures, FIG. 1 is a diagram that illustrates an imaging system 10 for acquiring and processing image data. In the illustrated embodiment, system 10 is a computed tomography (CT) system designed to acquire X-ray projection data, to reconstruct the projection data into a tomographic image, and to process the image data for display and analysis. Though the imaging system 10 is discussed in the context of medical imaging, the techniques and configurations discussed herein are applicable in other non-invasive imaging contexts, such as baggage or package screening or industrial nondestructive evaluation of manufactured parts. In the embodiment illustrated in FIG. 1, the CT imaging system 10 includes an X-ray source 12. As discussed in detail herein, the source 12 may include one or more conventional X-ray sources, such as an X-ray tube, or a distributed source configured to emit X-rays from different locations along a surface. For example, the source 12 may include one or more addressable solid-state emitters. Such solid-state emitters may be configured as arrays of field emitters, including one-dimensional arrays, i.e., lines, and two-dimensional arrays. In certain embodiments, the X-ray source 12 and/or collimator 14 may also include or incorporate various filters, such as a bowtie filter configured to provide variable degrees of X-ray attenuation to compensate for the varying observed thickness of a patient at different angular positions relative to the imaging system 10.

The source 12 may be positioned proximate to a collimator 14. The collimator 14 may consist of one or more collimating regions, such as lead or tungsten shutters, for each emission point of the source 12. The collimator 14 typically defines the size and shape of the one or more X-ray beams 16 that pass into a region in which a subject or object is positioned. In one embodiment where the operating voltage of the source 12 is being measured, the object being imaged may be an attenuation phantom 18, as presently depicted. Each X-ray beam 16 may be generally fan-shaped or cone-shaped, depending on the configuration of the detector array and/or the desired method of data acquisition. An attenuated portion 20 of each X-ray beam 16 passes through the subject or object, e.g., phantom 18, and impacts a detector array, represented generally at reference numeral 22.

The detector 22 is generally formed by a plurality of detector elements that detect the X-ray beams 16 after they pass through or around a subject or object placed in the field of view of the imaging system 10. Each detector element produces an electrical signal that represents the intensity of the X-ray beam incident at the position of the detector element when the beam strikes the detector 22. Alternatively, each element of detector 22 may count incident photons in the X-ray beam and may also determine their energy. During normal operation, the X-ray beam 16 is generated and the corresponding electrical signals are typically acquired at a variety of angular positions around the subject of interest so that a plurality of radiographic projection views can be collected. In one present embodiment where the operating voltage associated with the source 12 is being measured, scan data may be collected at only one or a limited number of angular positions, i.e., no or limited rotation of the source 12 occurs during data collection. Alternatively, in other embodiments scan data may be collected while rotating the source 12 and detector 22, such as might occur in a standard imaging context. In either embodiment, the electrical signals are acquired and processed to generate one or more scan datasets, as discussed in further detail below.

A system controller 24 commands operation of the imaging system 10 to execute examination and/or calibration protocols and to process the acquired data. The source 12 is typically controlled by a system controller 24. Generally, the system controller 24 furnishes power, focal spot location, control signals and so forth, for the CT examination sequences. The detector 22 is coupled to the system controller 24, which commands acquisition of the signals generated by the detector 22. The system controller 24 may also execute various signal processing and filtration functions, such as initial adjustment of dynamic ranges, interleaving of digital image data, and so forth. In the present context, system controller 24 may also include signal processing circuitry and associated memory circuitry. As discussed in greater detail below, the associated memory circuitry may store programs, routines, and/or encoded algorithms (including programs, routines, and/or algorithms for measuring voltage, as described herein) executed by the system controller 24, configuration parameters, image data, and so forth. In one embodiment, the system controller 24 may be implemented as all or part of a processor-based system such as a general purpose or application-specific computer system.

In the illustrated embodiment of FIG. 1, the system controller 24 may control the movement of a linear positioning subsystem 28 and a rotational subsystem 26 via a motor controller 32. In an embodiment where the imaging system 10 includes rotation of the source 12 and/or the detector 22, the rotational subsystem 26 may rotate the source 12, the collimator 14, and/or the detector 22 about the subject 18. It should be noted that the rotational subsystem 26 might include a gantry comprising both stationary components (stator) and rotating components (rotor). In embodiments comprising a stationary source 12 and a stationary detector 22, the rotational subsystem 26 may not cause mechanical motion, but may instead cause angularly displaced stationary emitters to be differentially activated to simulate rotation of the source 12 and detector 22. As noted above, in certain embodiments of the present technique for measuring source voltage, no or limited rotation of the source 12 and detector 22 (simulated or actual) occurs. Thus, in such embodiments, the rotational subsystem 26 may execute a protocol that holds the source 12, collimator 14, and detector 22 fixed in place, such as at an angular position designated by the voltage measurement protocol. However, in other embodiments for measuring voltage, the rotational subsystem 26 may rotate the source 12 and detector 22 such that the source 12 and detector are angularly displaced during the data acquisition process.

The linear positioning subsystem 28 may linearly displace a table or support on which the subject or object being imaged is positioned. Thus, the table or support may be linearly moved within the gantry or within an imaging volume (e.g., the volume located between the source 12 and the detector 22) and enable the acquisition of data from particular areas of the subject or object and, thus the generation of images associated with those particular areas. Additionally, the linear positioning subsystem 28 may displace one or more components of the collimator 14, so as to adjust the shape and/or direction of the X-ray beam 16. Further, in embodiments in which the source 12 and the detector 22 are configured to provide extended or sufficient coverage along the z-axis (i.e., the axis generally associated with the length of the patient table or support and/or with the lengthwise direction of the imaging bore) and/or in which the linear motion of the subject or object is not required, the linear positioning subsystem 28 may be absent.

As will be appreciated by those skilled in the art, the source 12 may be controlled by an X-ray controller 30 disposed within the system controller 24. The X-ray controller 30 may be configured to provide power and timing signals to the source 12. In addition, in some embodiments the X-ray controller 30 may be configured to selectively activate the source 12 such that tubes or emitters at different locations within the system 10 may be operated in synchrony with one another or independent of one another.

Further, the system controller 24 may comprise a data acquisition system (DAS) 34. In one embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a processor-based system, such as a computer 36. Alternatively, in other embodiments, the detector 22 may convert the sampled analog signals to digital signals prior to transmission to the data acquisition system 34.

In the depicted embodiment, a computer 36 is coupled to the system controller 24. The data collected by the data acquisition system 34 may be transmitted to the computer 36 for subsequent processing. For example, the data collected from the detector 22 may undergo pre-processing and calibration at the data acquisition system 34 and/or the computer 36 to produce representations of the line integrals of the attenuation coefficients of the subject or object (e.g., phantom 18) undergoing imaging. In one embodiment, the computer 36 contains data processing circuitry 37 for filtering and processing the data collected from the detector 22. In one embodiment, the data may be processed, in accordance with the operations and/or algorithms described herein, by the processing circuitry 37 to derive a measured value of the operating voltage associated with the source 12. Such a measured voltage may then be used to evaluate the operation of the source 12 and/or the imaging system 10, such as for regulatory compliance.

The computer 36 may include or communicate with a memory 38 that can store data processed by the computer 36, data to be processed by the computer 36, or routines and/or algorithms to be executed by the computer 36, such as for processing scan data to derive a measurement of the associated source voltage. It should be understood that any type of computer accessible memory device capable of storing the desired amount or type of data and/or code may be utilized by the imaging system 10. Moreover, the memory 38 may comprise one or more memory devices, such as magnetic, solid state, or optical devices, of similar or different types, which may be local and/or remote to the system 10. The memory 38 may store data, processing parameters, and/or computer programs comprising one or more routines for performing the processes described herein.

The computer 36 may also be adapted to control features enabled by the system controller 24 (i.e., scanning operations and data acquisition). Furthermore, the computer 36 may be configured to receive commands and scanning parameters from an operator via an operator workstation 40 which may be equipped with a keyboard and/or other input devices. An operator may, thereby, control the system 10 via the operator workstation 40. Thus, the operator may observe from the computer 36 a reconstructed image, a measured voltage, and/or other data relevant to the system 10. Likewise, the operator may initiate imaging or calibration routines, select and apply image filters, and so forth, via the operator workstation 40.

As illustrated, the system 10 may also include a display 42 coupled to the operator workstation 40. In one embodiment, the display 42 may be utilized to observe one or more screens displaying the results of a voltage measurement operation, as described herein. Additionally, the system 10 may include a printer 44 coupled to the operator workstation 40 and configured to print such voltage measurement results. The display 42 and the printer 44 may also be connected to the computer 36 directly or via the operator workstation 40. Further, the operator workstation 40 may include or be coupled to a picture archiving and communications system (PACS) 46. It should be noted that PACS 46 might be coupled to a remote system 48, radiology department information system (RIS), hospital information system (HIS) or to an internal or external network, so that others at different locations can gain access to the image data.

Although only one operator workstation is depicted, one or more operator workstations 40 may be linked in the system 10 for outputting system parameters, initiating scan protocols, viewing images, and so forth. In general, displays 42, printers 44, workstations 40, and similar devices supplied within the system 10 may be local to the data acquisition components, or may be remote from these components, such as elsewhere within an institution or hospital, or in an entirely different location, linked to the image acquisition system 10 via one or more configurable networks, such as the Internet, virtual private networks, and so forth.

In an embodiment where operating voltage of the source 12 is measured, an attenuating structure may be scanned as part of the measurement process. For example, referring now to FIG. 2, an attenuator phantom 18 is depicted which is separate from the imaging system 10 and which may be used in the voltage measurement process described herein when placed within the imaging system 10. The attenuator phantom 18 is formed from an X-ray attenuating substance (copper, aluminum, graphite, and so forth) and is sized to provide the desired degree of X-ray attenuation for the range of operational voltages employed by the imaging system 10. In one embodiment the attenuator phantom 18 includes alignment markings 60 such that the attenuator phantom 18 may be aligned and leveled in all three dimensions (e.g., in the axial, sagittal, and coronal planes) when placed within the imaging system 10. In one embodiment, the attenuator phantom 18 is an aluminum block having dimensions of 70 mm×60 mm×30 mm±0.025 mm. In such an embodiment, the attenuator phantom 18 may be a Type 1100-F material extruded in the X-direction and having a grain size less than 0.5 mm in both the Y- and the Z-directions.

Figure 2:
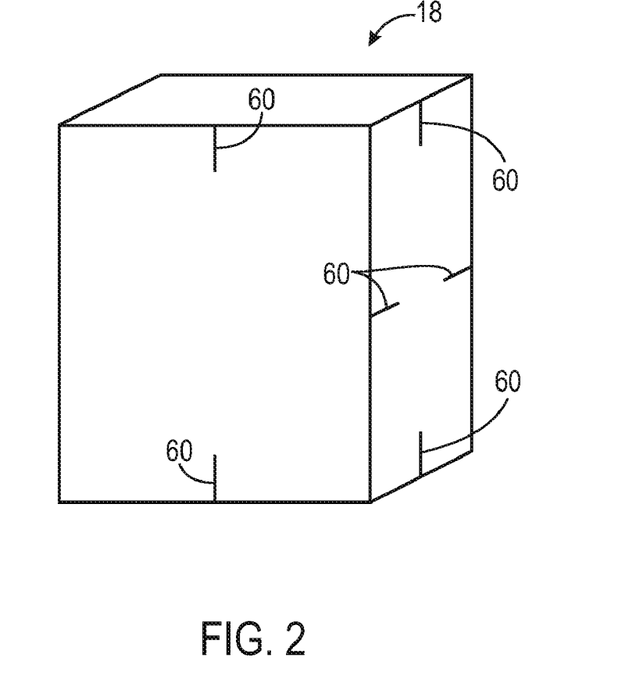
FIG. 2 depicts an attenuator phantom, in accordance with an embodiment of the present technique.

In other embodiments the attenuator phantom 18 may take other forms and/or may have other compositions. For example, the attenuator phantom 18 may be other geometric shapes than a rectangular block (e.g., a square block, a pyramidal or conical structure, a spherical or hemispherical structure, and so forth) including non-symmetric shapes. Likewise, the attenuator phantom may be composed of any suitable radiation attenuating material or combination of materials, including suitable metallic materials, non-metallic materials, composite materials, synthetic materials, and so forth.

Figure 3:
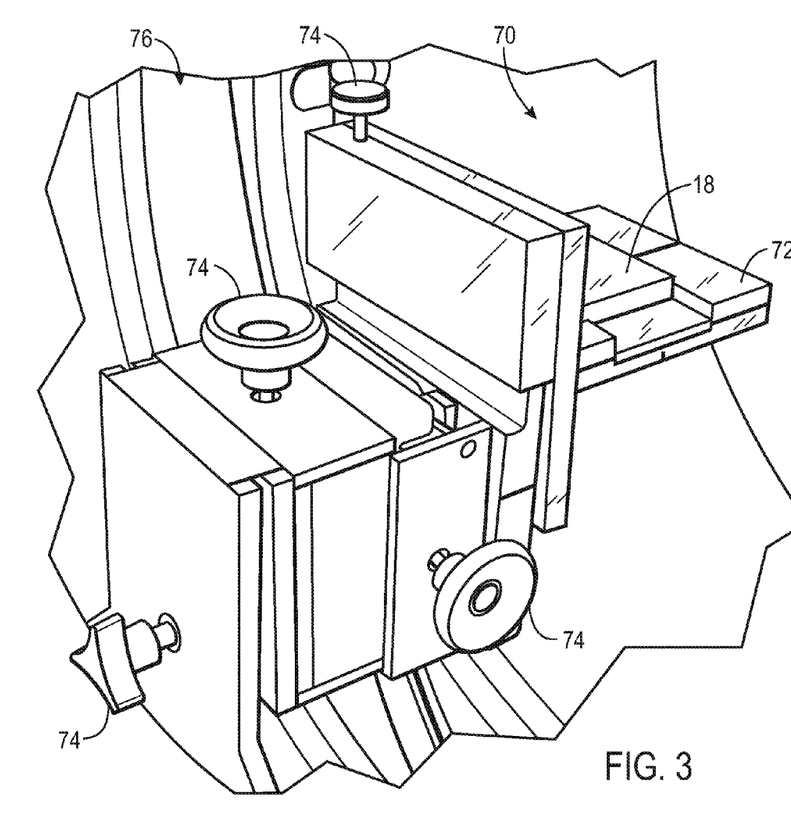
FIG. 3 depicts an attenuator phantom positioned within a CT imaging system, in accordance with an embodiment of the present technique.

As will be appreciated, the attenuator phantom 18 is a separate component that is placed within the imaging bore of the imaging system 10 to be scanned using a voltage measurement protocol. For example, referring to FIG. 3, the attenuator phantom 18 may be placed within the imaging bore 70 of a CT imaging system. In such an implementation, laser guides may be used to align and level the attenuator phantom 18 using the alignment markings 60 provided on the phantom 18. In the depicted implementation, the attenuator phantom 18 may be positioned on a holder 72 which positions the attenuator phantom at the desired location within the imaging bore 70, such as at the isocenter point associated with the imaging system 10. Based on the observed incidence of respective laser light guides relative to the alignment markings 60, various adjustment controls, such as the depicted knobs 74, may be adjusted to align the markings 60 with the incident laser light guides. In this manner, the attenuator phantom 18 may be aligned and leveled with respect to the imaging system 10. In addition, in the depicted embodiment, a liner (such as a mylar liner) typically covering a scan window 76 has been removed. In some implementations, this type of liner may contribute to X-ray attenuation variability and it may, therefore, be desirable to remove the liner as part of the voltage measurement protocol.

Figure 4:
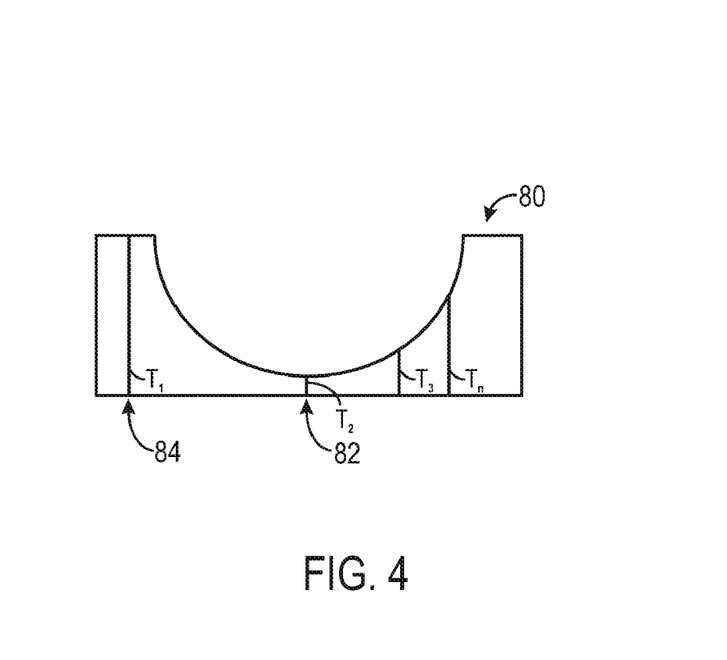
FIG. 4 depicts a bowtie filter, in accordance with an embodiment of the present technique.

Turning to FIG. 4, in another embodiment the attenuating structure may be a bowtie filter 80 provided as part of the X-ray source 12 or source collimator 14 of the imaging system 10, i.e., the bowtie filter 80 is typically a fixed component of the imaging system 10. The bowtie filter 80 may be composed of different thicknesses ($t_1$, $t_2$, $t_3$, ... $t_n$) of one or more than one attenuating materials, such as aluminum, graphite, and/or Teflon. For example, in one embodiment in which a bowtie filter 80 is composed of both aluminum and graphite, the path lengths of aluminum and graphite through the center of the medium filter are 0.2650 mm (or 0.2520 mm) and 1.9981 mm, respectively. In one such embodiment, the path lengths of aluminum and graphite through the edge of the filter are 7.2014 mm and 57.0970 mm, respectively. Further, in one embodiment, the filter may include a 75 µm layer of copper along part or all of the filter surface.

As discussed herein, the percent of X-rays transmitted through the center 82 of the bowtie filter 80 relative to the edge 84 of the bowtie filter 80 varies with the kV used to generate the X-rays at the source 12. For example, at 80 kV the percent of X-rays transmitted through the center 82 of the bowtie filter 80 compared to the edge 84 of the bowtie filter 80 is greater than at 120 kV. Thus, the center to edge attenuation ratio decreases as kV is increased. In embodiments in which a bowtie filter is employed, this relationship may be used to measure kV by acquiring X-ray attenuation data at both the center 82 and the edge 84 of the bowtie filter 80 using X-rays generated at one or more kV levels.

More generally, the ratio of the measured attenuation produced by two attenuators can be employed to measure changes in kV. In the context of a bowtie filter 80, the two attenuators may be the center 82 and the edge 84 of the bowtie filter. In the context of an attenuator phantom 18, the two attenuators may be the phantom 18 and air (i.e., the absence of the phantom 18). In such embodiments, source kV may be measured by associating the ratios of attenuation for the respective attenuator pairs with known kVs, such as via empirical testing and/or mathematical curve fitting.

With the foregoing in mind, FIGS. 5-9 depict various acts that may be performed in measuring voltage in accordance with embodiments of the present technique. For example, referring to FIG. 5, a flowchart is provided depicting acts that may be performed to when using a attenuator phantom 18 to measure voltage. As depicted in the flowchart, a table and/or gantry may be positioned (block 100) in preparation for the voltage measurement. For example, the gantry may be positioned such that the X-ray source 12 is at a default or home position, such as directly above the table. Likewise, the table may be positioned outside of the imaging bore of the imaging system 10 or at a location suitable for positioning the attenuator phantom 18, and/or a holder of the phantom 18, at a suitable position within the imaging bore. The positioning of the gantry and/or table may be performed automatically when a user initiates a voltage measurement application or routine.

Figure 5:
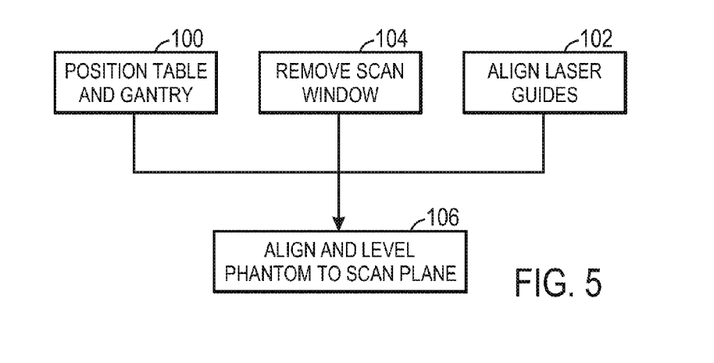
FIG. 5 depicts a flowchart relating acts associated with positioning an attenuator phantom within a CT imaging system, in accordance with an embodiment of the present technique.

In addition, an alignment or calibration of laser light guides (block 102) may be performed if such guides are present as part of the imaging system 10. For example, an alignment or calibration routine may be executed, with an operator providing feedback and/or positioning an alignment target as directed. In addition, if a liner or scan window that may contribute to attenuation is present in the imaging system 10, such as a mylar liner, the liner may be removed as part of the preparation for voltage measurement.

Once the imaging system 10 is prepared for the voltage measurement protocol, the attenuator phantom 18 is positioned within the imaging system 10, such as within the imaging bore. In particular, the attenuator phantom 18 is aligned and leveled with respect to the imaging system 10, such as by using laser light guides associated with the imaging system 10 and alignment markings 60 provided on the attenuator phantom 18. As a result of the alignment and leveling of the attenuator phantom 18 with respect to the imaging system 10, during a data acquisition of the voltage measurement process, a region of interest (ROI) within attenuator phantom 18 will be associated with projections of equal length. That is X-rays passing through the region of interest of the phantom 18 will pass through the same length of attenuating material, e.g., aluminum or copper. In this manner, one possible source of attenuation variation that is not attributable to the operating voltage of the source 12 may be addressed and/or eliminated.

Figure 6:
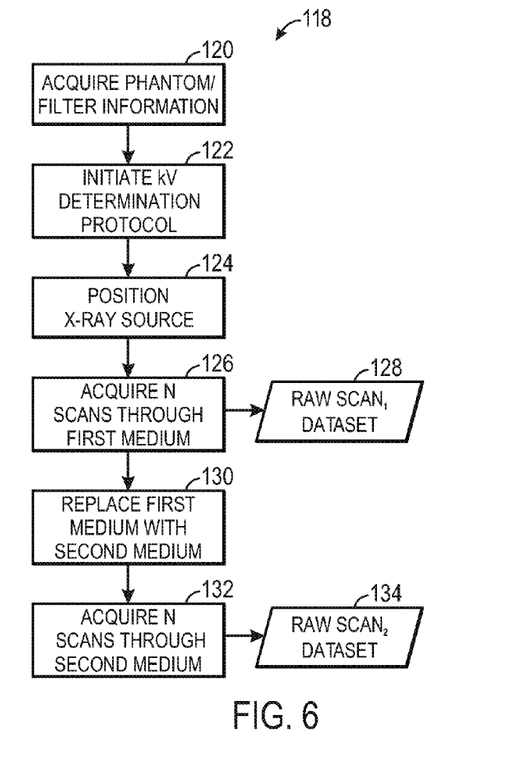
FIG. 6 depicts a flowchart relating acts associated with acquiring attenuation scan data, in accordance with an embodiment of the present technique.

Regardless of whether an attenuator phantom 18 or bowtie filter 80 is used as the attenuating medium, attenuation data is collected, as depicted by the method 118 outlined in flowchart form in FIG. 6. In one implementation, identification information about the attenuating medium, such as a serial number or other identifier for a phantom 18 or bowtie filter 80, may be acquired (block 120). Such information may be acquired for administrative purposes, such as to generate a report related to the voltage measurement event for regulatory or archival purposes.

A voltage measurement protocol may be initiated (block 122) in which the attenuation data is acquired. In certain embodiments, the protocol may be an automated process that proceeds automatically with data acquisition once initiated by an operator. As part of the protocol, the X-ray source 12 may be positioned (block 124), such as at the top of the gantry, if it has not already been moved to the correct location. As noted herein, in certain implementations data acquisition occurs with the X-ray source 12 positioned at one location (such as at the top of the gantry), with no rotation or other movement of the X-ray source 12 during data acquisition. In one embodiment, N scans of data 128 are acquired (block 126) through a first attenuating medium, such as air or an attenuator phantom 18 in one embodiment or the center 82 or edge 84 of a bowtie filter 80 in another embodiment. In one implementation, four scans are taken of the first attenuating medium, such as respective scans at 80 kV, 100 kV, 120 kV, and 140 kV, with each scan constituting a respective raw $scan_1$ dataset 128. Further, in one such implementation, the mA used in operating the X-ray source 12 is kept constant and at a low value (e.g., approximately 50 mA) to reduce ripple effects.

After data acquisition using the first attenuating medium, the first attenuating medium is replaced or adjusted (block 130) so that the second attenuating medium is in the scan path. For example, in an embodiment in which an attenuator phantom 18 is employed, if the first scan is of the phantom 18, the phantom 18 may then be removed so that the second scan is of air, i.e., the absence of the phantom 18. Conversely, if the first scan was of air, the attenuator phantom 18 may be positioned (including proper alignment and leveling as discussed herein) in the scan path for the second scan Likewise, if the attenuating medium is a bowtie filter 80, if the first scan was through the center 82 of the filter 80, the filter 80 may be moved or adjusted so that the second scan passes through the edge 84 of the bowtie filter 80. Conversely, if the first scan was through the edge 84 of the filter 80, the filter 80 may be moved or adjusted so that the second scan passes through the center 82 of the bowtie filter 80.

Once the second attenuating medium is positioned, N scans of data 134 are acquired (block 132) through a second attenuating medium at the same respective voltages as utilized in acquiring the first dataset 128. For example, in one implementation, four scans are taken of the second attenuating medium at respective voltages of 80 kV, 100 kV, 120 kV, and 140 kV and the data associated with these four scans constitutes respective raw $scan_2$ datasets 134. Thus, two or more respective datasets 128, 134 are generated using different attenuating media.

In one embodiment, the raw scan datasets 128, 134 for each attenuating medium and at each respective voltage level are each pre-processed to prepare the data for subsequent processing. As will be appreciated, each dataset 128, 134 is initially three-dimensional with the dimensions corresponding to detector rows and detector channels (e.g. rows and columns of detector elements), and to views. The view dimension corresponds to the time unit of data acquisition and, in imaging implementations where the source 12 and detector 22 rotate, may also correspond to the angular position at which the image data is acquired. However, in embodiments disclosed herein in which the source 12 and detector 22 do not rotate during the voltage measurement process, the view dimension does not vary with respect to angular position. For example, one view may correspond to one-second of data acquired with the source 12 and detector 22 at a fixed position. Such a one-second view may correspond to 984 trigger events, i.e., 984 data acquisitions.

Figure 7:
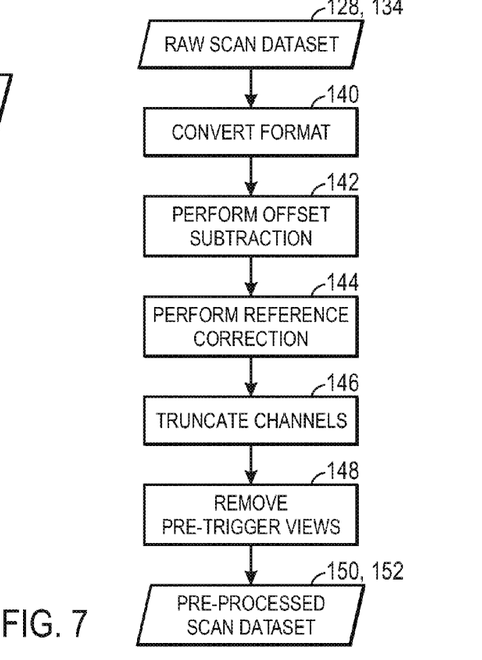
FIG. 7 depicts a flowchart relating acts associated with pre-processing of attenuation scan data, in accordance with an embodiment of the present technique.

Examples of acts that may be performed as part of such pre-processing are depicted in FIG. 7 in flowchart form. As will be appreciated, some or all of the depicted acts may be performed as part of the pre-processing routine. For example, in one implementation, each raw scan dataset 128, 134 undergoes a format conversion (block 140), such as to convert the datasets from a FFP or hybrid FFP format (i.e., a lossy compression scheme) to a floating point format. In addition, an offset image subtraction may be performed (block 142) on the datasets 128, 134. Such a subtraction may remove noise by subtracting a dark image (i.e., the DAS/detector channel signal output when no X-rays are being generated, also known as the offset or dark current) from the acquired image data (i.e., the DAS/detector channel signal output when X-rays are being generated).

In addition, other pre-processing may be performed on the raw scan datasets 128, 134 to prepare the datasets for subsequent processing. For example, a reference correction may be performed (block 144). In one such implementation, the data channels may be divided by corresponding data values stored in a detector left reference channel, where the stored data values relate to noise data. In addition, channel truncation may be performed (block 146) in which non-image generating channels (such as end channels and other non-image channels) may be removed from the datasets 128, 134. Likewise, initial views acquired at the beginning of the scan sequence, i.e., pre-trigger views, included in each dataset 128, 134 may be removed (block 148). As a product of some or all of these processing steps, pre-processed scan datasets 150, 152 for each attenuating medium and at each respective voltage level are generated.

Figure 8:
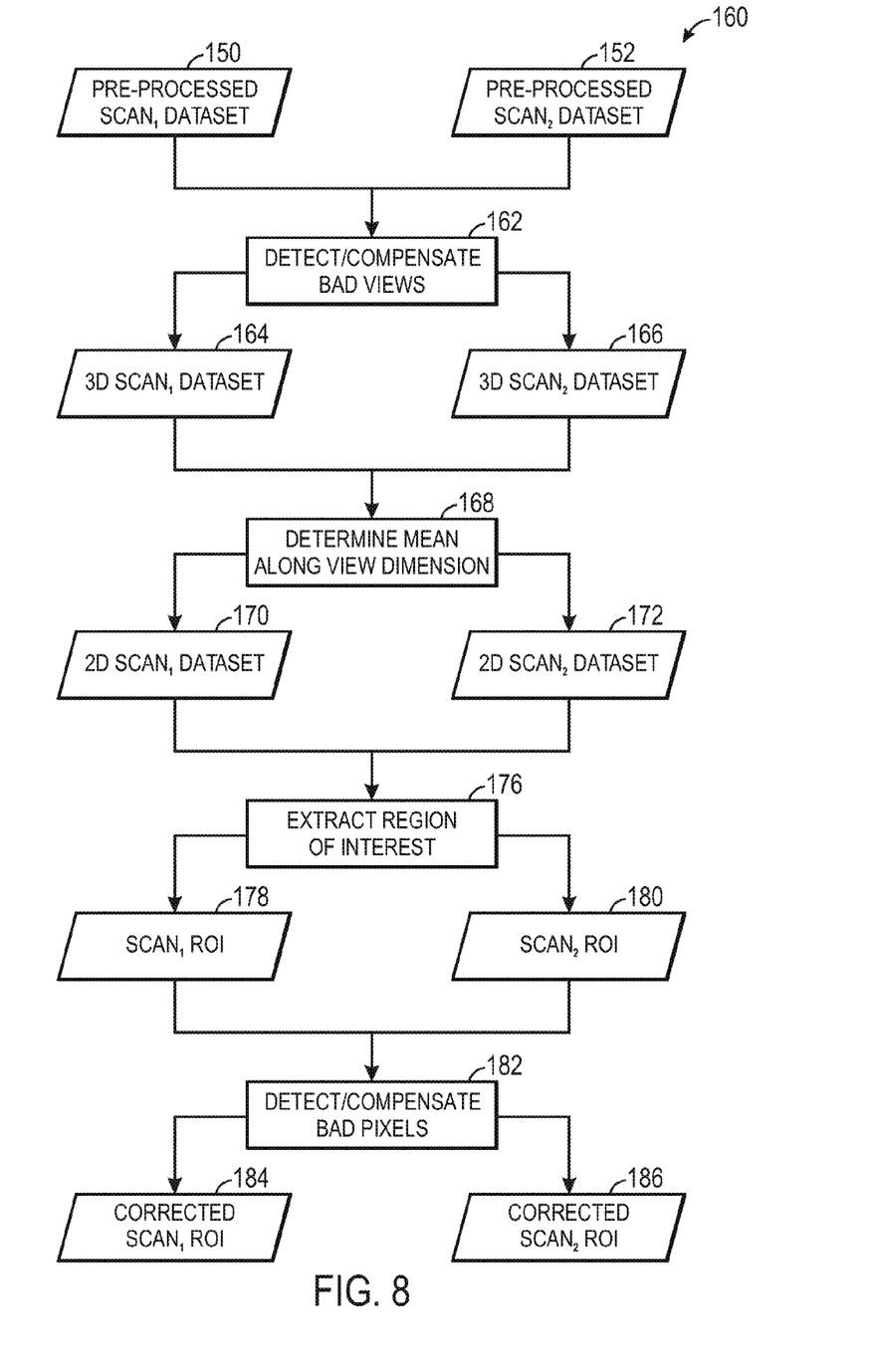
FIGS. 8-9 depicts a flowchart relating acts associated with processing attenuation scan data to generate a measured voltage, in accordance with an embodiment of the present technique.
Figure 9:
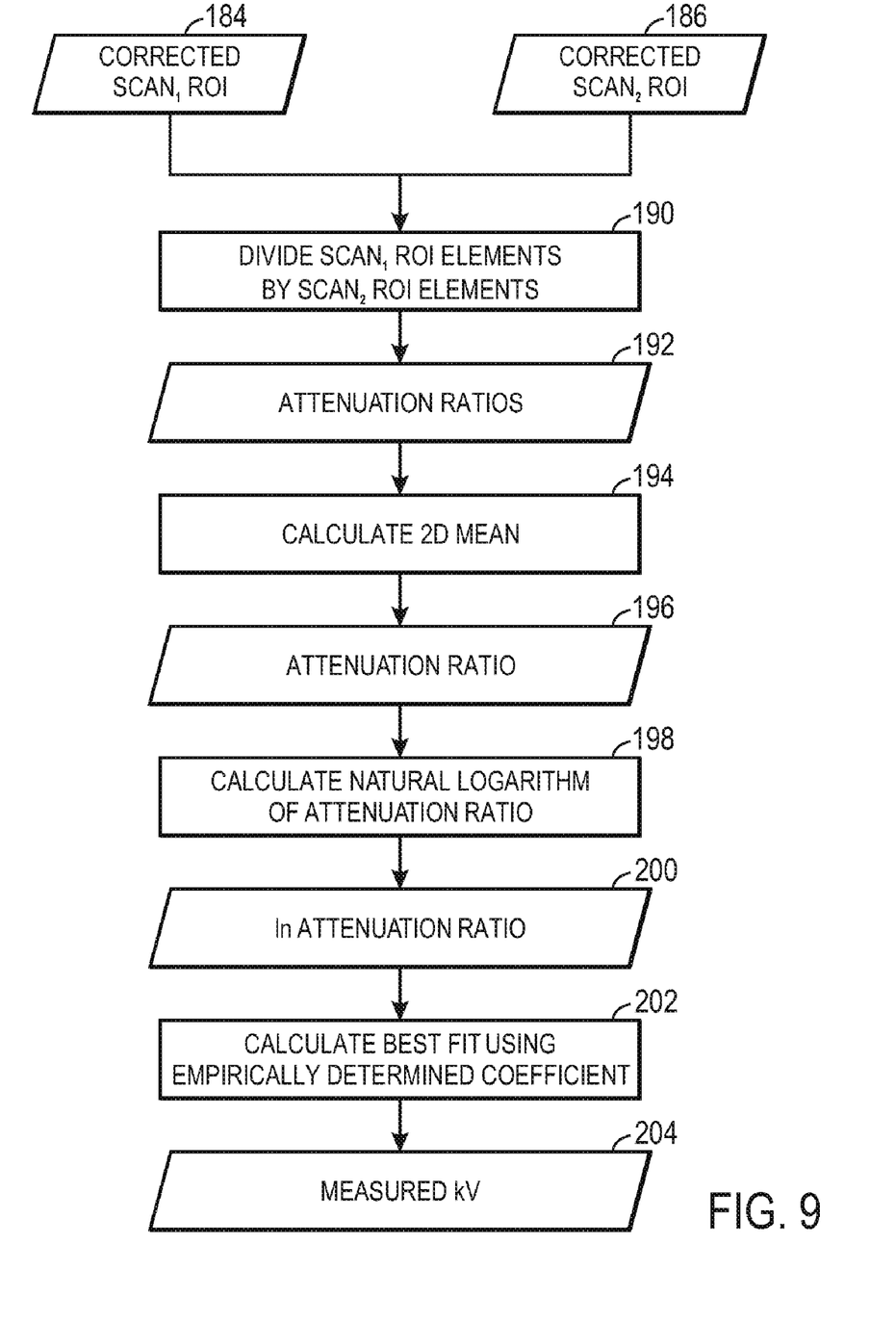

Turning to FIGS. 8 and 9, an algorithm 160 for measuring a source voltage using the pre-processed scan datasets 150, 152 is depicted in flowchart form. In accordance with one embodiment of this algorithm, the pre-processed $scan_1$ dataset 150 and the pre-processed $scan_2$ dataset 152 at a given voltage level are each evaluated for bad view data and any view data determined to be bad (such as by reference to a threshold criterion or statistical quality measure) is removed (block 162) to generate 3D $scan_1$ dataset 164 and 3D $scan_2$ dataset 166. For example, views containing corrupted data, such as data corrupted due to tube spits during image acquisition, may be removed from the pre-processed scan datasets 150, 152 to generate the 3D scan datasets 164, 166. In one implementation, view data from both scan datasets 150, 152 is removed for any kV/View value greater than some threshold (e.g. 10%) relative to the kV selection used to generate the respective datasets. In such embodiments, a warning or alert may be generated if more than some threshold amount (e.g., 10%) of view data is removed.

In the depicted implementation, the 3D scan datasets 164, 166 are converted to 2D scan datasets 170, 172 by taking the mean along the view dimension (block 168). That is, the data in each 3D scan dataset 164, 166 may be averaged across views to generate the 2D scan datasets 170, 172 that vary along the row and channel dimensions but not along the view dimension, which is assigned a constant value corresponding to the average of the views. Such a conversion may be useful in embodiments in which no rotation of the source 12 and detector 22 occurs during data acquisition as the view dimension does not reflect any differences in angular position in the acquired data, but instead only reflects the differential acquisition timing. Thus, in such embodiments, the view dimension may be simplified to a single value, such as the mean value, to reduce the respective datasets to two-dimensions. As will be appreciated, other techniques for collapsing the view dimension may be employed such as using the mode or median value or some of measure of central tendency.

In the depicted embodiment, a respective scan region of interest (ROI) 178, 180 is extracted (block 176) from each 2D scan dataset 170, 172 for further processing. The regions of interest 178, 180 may correspond to that image data acquired at the isocenter of the detector 22 where pixels are determined to be stable. For example, extraction of the regions of interest 178, 180 may involve removing two rows of data on each side of the acquired images to generate regions that are approximately 28 rows by 100 channels in size. In an embodiment in which the attenuating medium is an attenuator phantom 18, the regions of interest 178, 180 may correspond to image data representing the center of the phantom 18.

Each region of interest 178, 180 may be further processed to detect and compensate for bad pixels (block 182) identified within the regions of interest 178, 180. For example, in one embodiment mean pixel amplitude is determined in each region of interest 178, 180 and each pixel is evaluated to determine if the respective pixel is consistent with the mean, such as within one standard deviation of the mean. In an embodiment, the standard deviation may be defined as the minimum between five times the phantom region of interest standard deviation and 5% of the phantom region of interest mean value. The bad pixel detection and compensation process 182 may be iteratively performed until all remaining data is within the specified limits. Pixels determined to be bad, i.e., outside the specified one standard deviation or other boundary, are eliminated from their respective datasets to generate corrected scan ROI datasets 184, 186. In one embodiment, bad pixel counts above a threshold (e.g., 100) may cause a warning to be displayed Likewise bad pixel counts above a threshold (e.g., 1,000) may terminate the voltage measurement process and may result in the operator being instructed to realign and/or relevel the attenuator phantom 18 (as the bad pixels may be the result of a misalignment of the phantom 18) before reinitiating the voltage measurement operation.

Turning to FIG. 9, the first corrected scan ROI dataset 184 is divided (block 190) by the second corrected scan ROI dataset 186 on an element by element (e.g., pixel by pixel) basis to generate an attenuation ratio 192 for each element (e.g., pixel). For example, in one embodiment employing an attenuator phantom 18, a corrected air ROI dataset may be divided pixel by pixel by a corrected phantom ROI dataset to generate the attenuation ratios 192. In another embodiment in which a bowtie filter 80 is the attenuating medium, a corrected center filter ROI dataset may be divided pixel by pixel by a corrected edge filter ROI dataset to generate the attenuation ratios 192 for a given operating voltage (e.g., 80 kV, 100 kV, 120 kV, or 140 kV). As will be appreciated, which set of data is divided by which is largely arbitrary and may be varied as long as the impact on the calculated ratios is taken into account.

The array of attenuation ratios 192 derived on a pixel by pixel basis may be averaged (block 194) to generate a single, average attenuation ratio 196 for the respective operating voltage. The natural logarithm 200 of the attenuation ratio 196 may be taken (block 198) and fit mathematically (block 202) to derive a measured voltage value 204. For example, in an embodiment utilizing an attenuator phantom 18, a measured voltage 204 may be determined by fitting the natural logarithm 200 of the attenuation ratio 196 for a given voltage in accordance with an equation such as the following:

$$C_4X^4+C_3X^3+C_2X^2+C_1X^1+C_0 \qquad (1)$$

where the coefficients C are empirically derived for an imaging system model or type, such as during development of the model. For example, the coefficients C may be derived for equation (1) based on voltage measurements obtained using conventional techniques, e.g., use of a bleeder oscilloscope suitable for measuring high voltage, thus each operating voltage being measured may have its own calibration equation (1) and coefficients. Once the coefficients C are established, the attenuation measurements, as described herein, may be mathematically fit to the established curve to provide a measurement 204 of an operating voltage driving the X-ray source 12. The above algorithm 160 may be repeated for each voltage of interest (e.g., 80 kV, 100 kV, 120 kV, or 140 kV) to generate respective measured voltages 204 for each voltage level. In an embodiment employing a bowtie filter 80 as the attenuating medium, a second order polynomial equation describes kV as a function of the inverse natural logarithm of the respective attenuation ratio 196. For embodiments employing an attenuator phantom 18 as the attenuating medium, a first order polynomial describes kV as a function of the inverse natural logarithm of the respective attenuation ratio 196.

While the above describes one example of an implementation in which acquired image data is used to calculate an operating voltage of a radiation source, it should be appreciated that certain aspects of the implementation may be varied while still allowing a voltage to be measured. For example, the order of certain steps may be altered without affecting the resulting voltage measurement. For instance, the three-dimensional datasets may be reduced in dimension in different ways or at different times in the process of deriving the attenuation ratio 196 without affecting the voltage measurement 204. Thus, individual ratios from the three-dimensional datasets could be averaged to generate an attenuation ratio 196. Alternatively, the three-dimensional data could be averaged to generate two-dimensional datasets, one-dimensional datasets, and/or a scaler. The averages for the two different attenuating materials could be derived using the respective reduced dimension datasets and the respective ratio of the averages could be determined. Further, in one embodiment, two-dimensional datasets (instead of three-dimensional datasets) may be initially acquired with a long integrated exposure. In general, various implementations may be employed which allow sufficient photons to be collected so that a suitable signal-to-noise ratio is attained for the voltage measurement process. This may be accomplished by averaging of the datasets to reduce the dimensionality of the data, as discussed herein, regardless of the manner in which or the time at which the averaging step or steps are performed.

Figure 10:
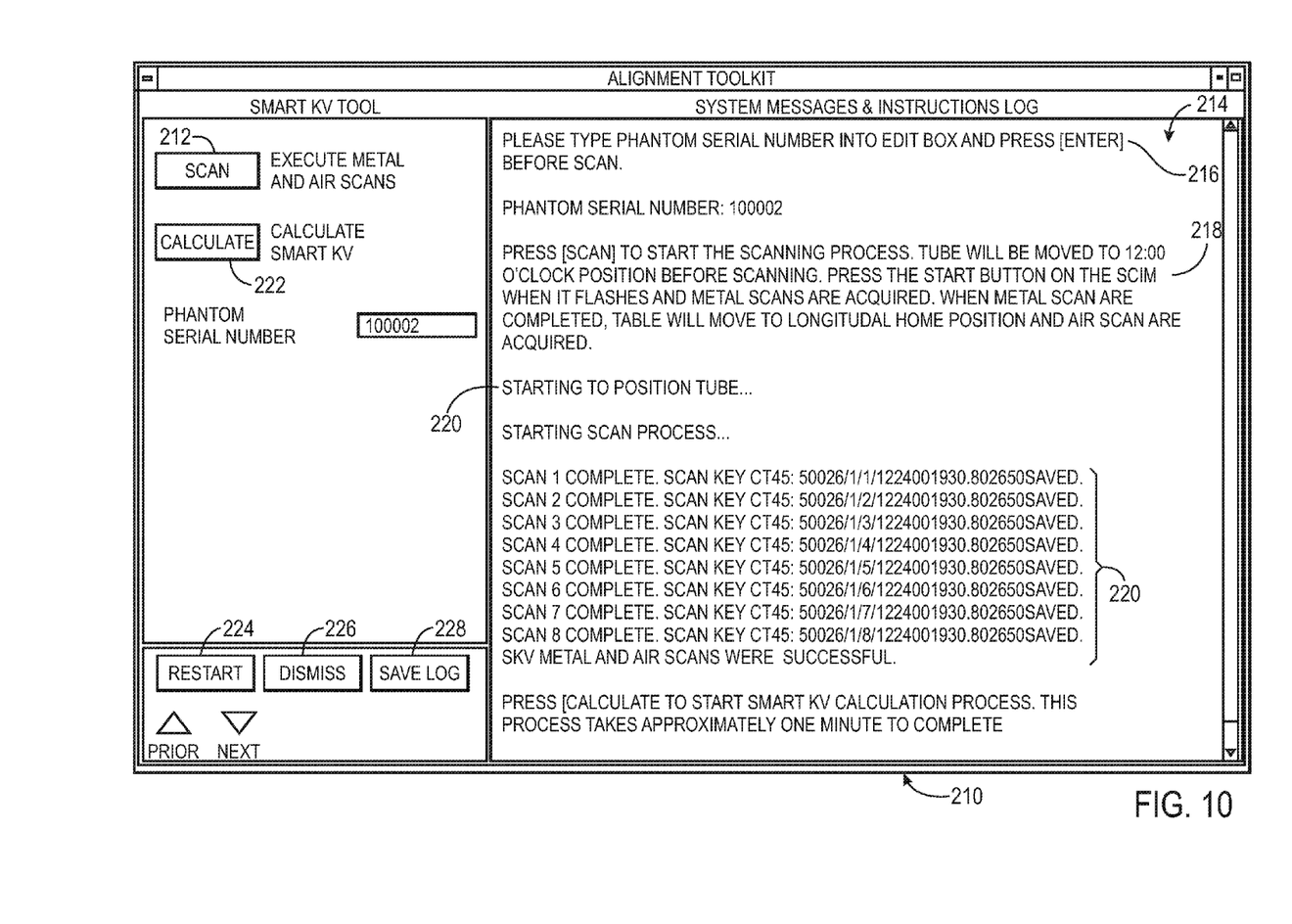
FIG. 10 depicts an example of a scan data acquisition screen, in accordance with an embodiment of the present technique.
Figure 11:
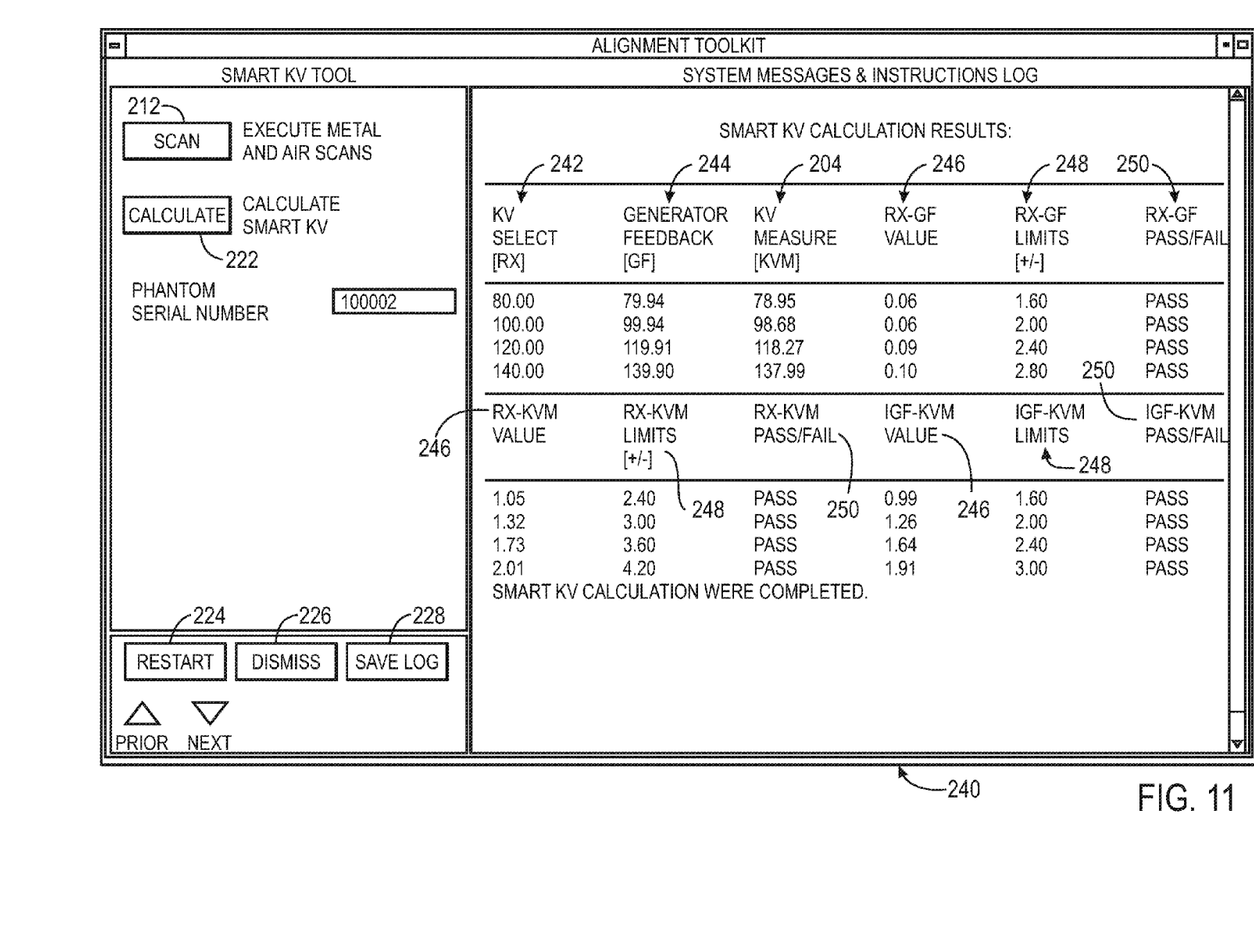
FIG. 11 depicts an example of a results screen, in accordance with an embodiment of the present technique.
Figure 12:
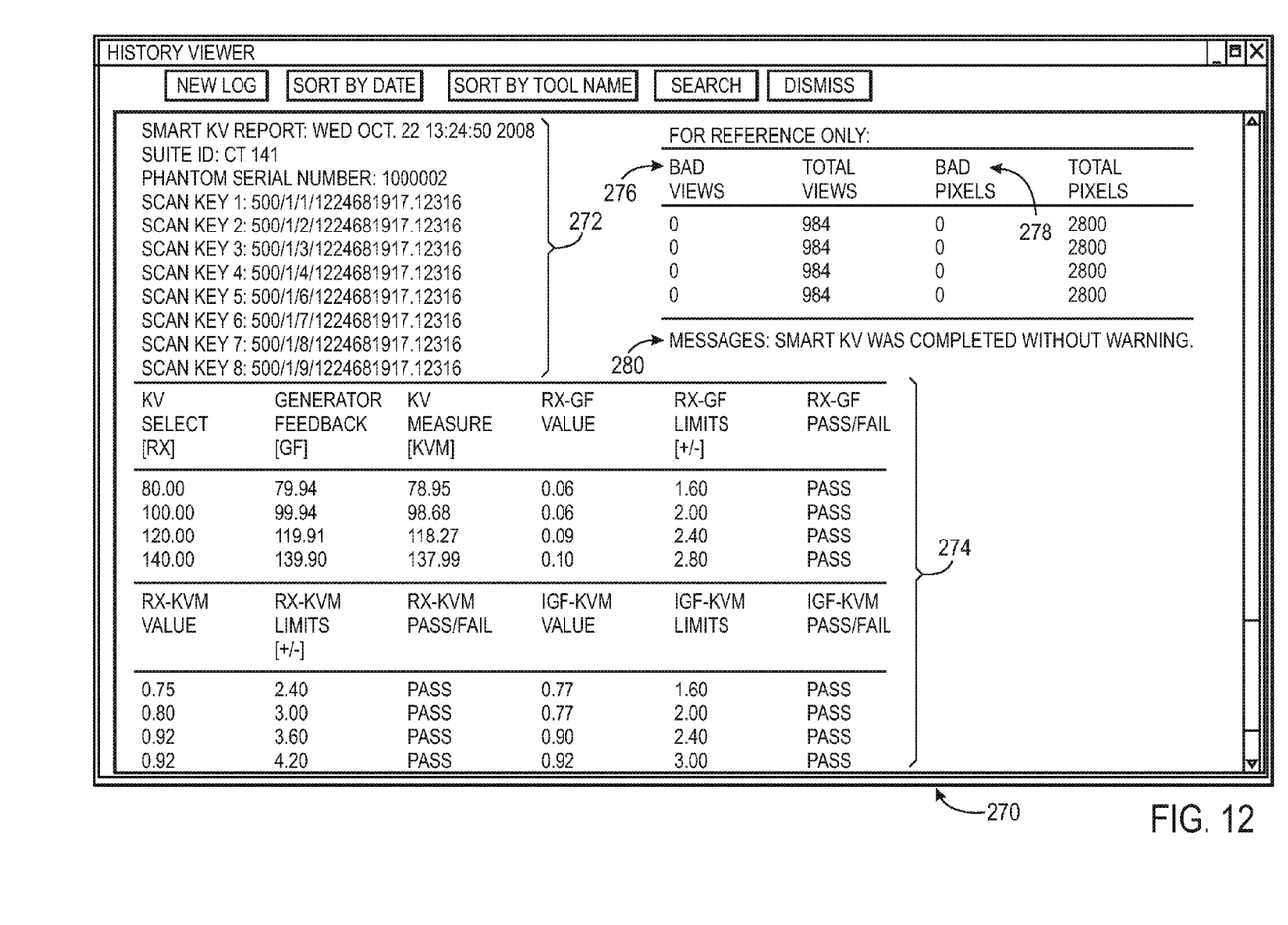
FIG. 12 depicts an example of a log screen, in accordance with an embodiment of the present technique.

With the foregoing in mind, FIGS. 10-12 depict sample screenshots of an application suitable for measuring voltage in accordance with the presently disclosed technique. For example, FIG. 10 depicts an example of an application screen 210 that may be displayed as part of a scanning process used acquire attenuation data used to measure four respective voltages. As depicted in this example screen 210, a scan button 212 is provided that may be selected by an operator to initiate the automated scanning of an attenuator phantom 18 and air or of the center 82 and edge 84 of a bowtie filter 80. In the depicted example, the scan button 212 is illustrated as having already been selected. An information screen 214 displays various instructions and updates as to the status of the scans. For example, the information screen 214 may display a prompt 216 asking a user to input a phantom serial number and instructions 218 on how to initiate the scan process. In addition, the information screen 214 may provide updates, including updates 220 about the positioning of the X-ray tube and updates indicating that the various scans of the phantom 18 and air are complete at each specified voltage level. For example, the eight depicted updates 220 convey that the phantom and air were each scanned four times (i.e., at 80 kV, 100 kV, 120 kV, and 140 kV). Also displayed on the screen 210 are other possible operator selectable options, such as an option 222 to proceed to calculate the measured voltages, an option 224 to restart the voltage measurement process, an option 226 to exit the voltage measurement process, and an option 228 to save a log file (such as a text file) of the voltage measurement operation.

Turning to FIG. 11, an example of a screenshot 240 displaying results of the voltage measurement process is depicted. For example, in this example, the selected or prescribed voltages 242 (e.g., 80 kV, 100 kV, 120 kV, and 140 kV) are displayed along with the measured voltages 204. In addition, the measured generator feedback 244 and various difference measures 246 based on these measured and prescribed values are displayed. Further, information concerning the tolerances, i.e., limits 248 for the various difference measures may be displayed so that an operator can view what would constitute passing or failing for a category of measurements. In addition, actual qualitative indications 250 of whether a measurement has failed (i.e., is outside the specified tolerances) may also be displayed, allowing an operator to quickly assess whether any failure events occurred during the voltage measurement event.

Turning to FIG. 12, an example of a log screen 270 that may be printed or stored (such as in a text file) by the voltage measurement application is provided. In this example, various information from the scanning and results screens may be displayed or stored as part of the log screen 270. For example, information related to the scanning process 272 may be part of the log screen 270 along with the voltage measurement results 274. In addition, the log screen 270 may include information generated as part of the voltage measurement process, such as the number of bad views 276 and/or bad pixels 278, and or whether any warnings 280 were generated during the voltage measurement process.

Technical effects of the invention include the capability to indirectly measure a voltage used to generate X-rays in an imaging system. Technical effects also include the calculation of an operating voltage using attenuation data obtained for at least two different attenuating mediums. Technical effects also include the calculation of respective voltage measurements at one or more different prescribed voltage levels using differential attenuation data. Acquisition of attenuation scan data and/or calculation of the voltage measurements may be performed automatically as part of a voltage measurement application executed on a suitable processor-based system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for measuring voltage, comprising:
accessing a first scan dataset generated by transmitting radiation through an attenuation phantom and a second scan dataset generated without transmitting radiation through the attenuation phantom;
extracting a first region of interest from the first scan dataset and a second region of interest from the second scan dataset;
deriving a mean attenuation ratio corresponding to the mean attenuation observed in the first region of interest relative to the mean attenuation observed in the second region of interest; and
using the mean attenuation ratio or a value derived from the mean attenuation ratio to measure a voltage used to generate the first scan dataset and the second scan dataset.

2. The method of claim 1, comprising removing or compensating for bad views within the first scan dataset and the second scan dataset.

3. The method of claim 1, wherein the first scan dataset and the second scan dataset are three-dimensional.

4. The method of claim 3, comprising averaging the first scan dataset and the second scan dataset along one or more dimensions to reduce the first scan dataset and the second scan dataset to two-dimensions or to one-dimension.

5. The method of claim 1, comprising removing or compensating for bad pixels in the first region of interest and the second region of interest.

6. The method of claim 1, comprising:
dividing the first region of interest by the second region of interest on an element-by-element basis to generate a respective ratio for each element of the regions of interest;
calculating the mean attenuation ratio by averaging the respective ratios.

7. A voltage measurement system, comprising:
a processor-based system, comprising:
a memory storing executable instructions; and
processing circuitry configured to execute the executable instructions stored in the memory;
wherein the stored executable instructions include instructions which, when executed, cause:
acquisition of a first scan dataset and a second scan dataset by an imaging system, wherein the first scan dataset is generated by transmitting radiation through an attenuating phantom and the second scan dataset is generated without transmitting radiation through the attenuating phantom;
processing of the first scan dataset and the second scan dataset to generate an attenuation ratio; and
processing of the attenuation ratio to generate a measurement of a voltage used by the imaging system to generate the first scan dataset and the second scan dataset.

8. The voltage measurement system of claim 7, wherein the processor-based system comprises a component of the imaging system.

9. The voltage measurement system of claim 7, wherein the second scan dataset is generated by transmitting radiation through air instead of the attenuating phantom.

10. The voltage measurement system of claim 7, wherein the imaging system comprises a CT imaging system.

11. The voltage measurement system of claim 7, wherein processing of the first scan dataset and the second scan dataset includes compensating for one or more of bad views or bad pixels in the scan datasets.

12. The voltage measurement system of claim 7, wherein processing of the first scan dataset and the second scan dataset includes reducing the first scan dataset and the second scan dataset from three-dimensions to two-dimensions.

13. The voltage measurement system of claim 7, wherein processing of the first scan dataset and the second scan dataset includes extracting a respective region of interest from each of the first scan dataset and the second scan dataset.

14. The voltage measurement system of claim 7, wherein processing of the attenuation ratio comprises fitting a natural logarithm of the attenuation ratio to an empirically derived equation.

15. A non-transitory computer-readable medium comprising computer executable code for measuring voltage, the executable code encoding instructions for:

processing a first set of scan data and a second set of scan data to derive an attenuation ratio, wherein each set of scan data is generated using the same prescribed voltage to generate X-rays but wherein the X-rays used to generate first set of scan data are attenuated by an attenuation phantom and the X-rays used to generate the second set of scan data are not attenuated by the attenuation phantom;

processing the attenuation ratio to derive an indirect measurement of the voltage used to generate the X-rays; and comparing the indirect measurement of the voltage to the prescribed voltage.

16. The non-transitory computer-readable medium of claim 15, further comprising executable code encoding instructions for displaying a result of the comparison of the indirect measurement of the voltage to the prescribed voltage.

17. The non-transitory computer-readable medium of claim 15, further comprising executable code encoding instructions for acquiring the first set of scan data and the second set of scan data using an X-ray based imaging system.

18. The non-transitory computer-readable medium of claim 15, wherein the X-rays used to generate the second set of scan data are attenuated by air instead of the attenuation phantom.

* * * * *